United States Patent [19]

McDonald

[11] Patent Number: 5,009,644
[45] Date of Patent: Apr. 23, 1991

[54] NEEDLE PLACEMENT VERIFIER

[75] Inventor: Ray S. McDonald, St. Paul, Minn.

[73] Assignee: Medtronic, Inc., Minneapolis, Minn.

[21] Appl. No.: 385,132

[22] Filed: Jul. 25, 1989

[51] Int. Cl.$^5$ .............................................. A61M 5/32
[52] U.S. Cl. ...................................... 604/175; 604/93; 604/116
[58] Field of Search ................ 604/116, 117, 93, 175, 604/8–10, 131, 891; 116/DIG. 17, 205; 128/899

[56] References Cited

U.S. PATENT DOCUMENTS

| | | | |
|---|---|---|---|
| 4,216,775 | 8/1980 | Cottingham | 340/573 |
| 4,692,146 | 9/1987 | Hilger | 604/93 |
| 4,760,837 | 8/1988 | Petit | 604/93 |

OTHER PUBLICATIONS

Advertisement entitled "Celsite Implantable Vascular Access".

*Primary Examiner*—Stephen C. Pellegrino
*Assistant Examiner*—Ralph A. Lewis
*Attorney, Agent, or Firm*—S. A. Kassatly; Robert J. Klepinski; Reed A. Duthler

[57] ABSTRACT

The present invention includes an implantable medical device with needle sensing means. The sensing means employs the casing of the device, the body of the patient, and the needle in a circuit which activates electrical means for notifying the physician of needle placement. Contact of the hypodermic needle with the desired location in the reservoir completes a circuit which is activated by power means to provide preferably audible feedback.

5 Claims, 1 Drawing Sheet

NEEDLE PLACEMENT VERIFIER

FIELD OF THE INVENTION

The present invention relates to devices for determining needle placement with an implantable device, particularly in the reservoir of a drug dispensing device.

BACKGROUND OF THE INVENTION

Many implantable medical devices require percutaneous communication. For example, devices which dispense drugs within the body require a supply provided by hypodermic needle injection through the skin. In devices such as implantable drug dispensers or catheter access ports, a needle is inserted through the skin, through a pierceable septum on the drug dispenser and into a reservoir where the drug is to be injected.

Since the medical device is installed subcutaneously, care must be taken to make sure that the needle is properly placed into the device before injection. If the needle misses the device, drug will be dispensed in the body either in an improper location or in improper amounts. If the needle is not fully pierced to the septum, drug cannot be dispensed properly into the desired reservoir location.

Previous attempts have been made to provide notification of needle placement. These have involved complex apparatus such as the Celcontrol brand detector which requires the attachment of an electrode to the skin and the attachment of a wire to complete the circuit to the hypodermic needle. What is needed is a simpler technique for sensing needle position which does not require attachments to the skin or needle.

SUMMARY OF THE INVENTION

The present invention includes an implanted medical device with needle sensing means. The sensing means employs the casing of the device, the body of the patient, and the needle in a circuit which activates electrical means for notifying the physician of needle placement. Contact of the hypodermic needle with the desired location in the reservoir completes a circuit which is activated by power means to provide preferably audible feedback.

DETAILED DESCRIPTION OF THE PREFERRED EMBODIMENTS

Figure 1:
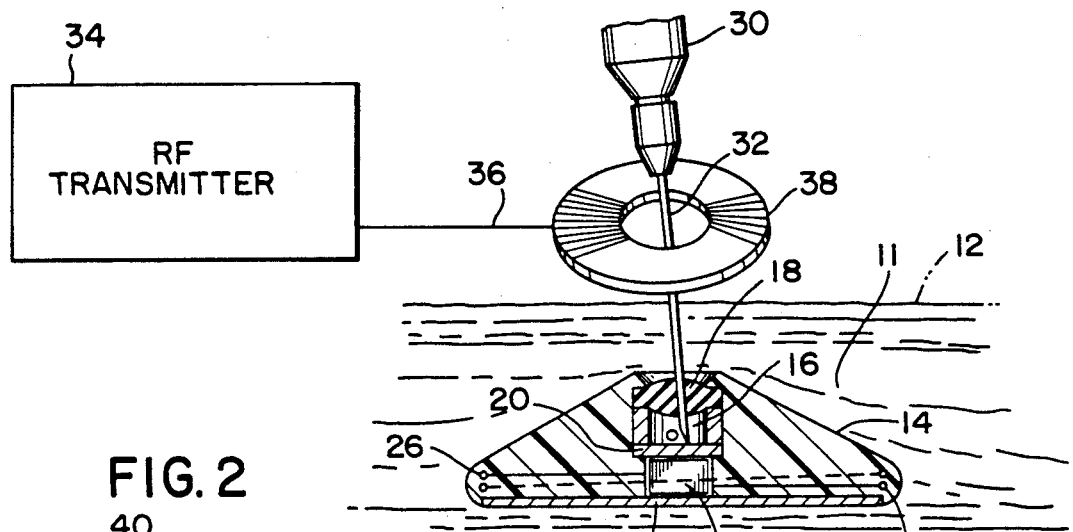
FIG. 1 is a system view, partly schematic, of an implantable apparatus constructed according to the present invention including an external RF transmitter in a hypodermic needle.

The invention is illustrated by a catheter access port 10 implanted in tissue 11 below skin 12 of a patient. One skilled in the art may employ the present invention and other devices requiring percutaneous contact with medical instruments. Access port 10 includes a body 14 which has a fluid reservoir 16. Reservoir 16 is sealed off from the patient environment by pierceable septum 18. Access port 10 includes a contact plate 20 at the base of reservoir 16. Contact plate 20 is electrically connected to circuitry 22, shown schematically in FIG. 1. Circuitry 22 is electrically connected to conductive base plate 24 which is mounted on the outside of body 14. Embedded in body 14 and electrically connected to circuit 22 is coil or receiving antenna 26.

Access port 10 is used to transmit medicament through a portion of the body by a catheter. Medicament is added to reservoir 16 by a syringe 30 having a needle 32 which pierces skin 12 and septum 18. In the position illustrated, needle 32 is within reservoir 16 in contact with contact 20 and is prepared for drug injection.

In order for the sensing means of access port 10, including circuitry 22, contact plate 20 and common plate 22 to sense placement of needle 32, power must be available. In this embodiment, power is transmitted by radio frequency. RF transmitter 34 is shown schematically connected by wires 36 to transmitting antenna 38. Components 34-38 are well known prior art devices which may be employed in the practice of the present invention. Transmitter 34 could be any of the available prior art transmitters. A particular useful example would be the transmitter for the Medtronic Pisces brand spinal stimulation system.

Antenna 38 is shown as a circular disk with a central hole, but may be other suitable medical transmitting antennas. When transmitter 34 sends RF energy through antenna 38, it is received by receiving antenna 26 within access port 10.

Figure 2:
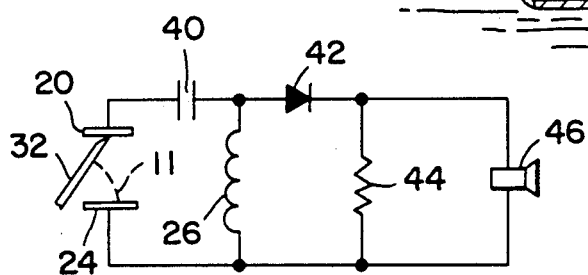
FIG. 2 is a schematic of a sample circuit for the device of FIG. 1.

Referring to FIG. 2, circuit 22 includes capacitor 40, diode 42, resistor 44 and piezoelectric beeper 46. Circuit 22 has capacitor 40 in series with coil 26. When no needle 32 is present, the only power present is the reactance of coil 26. Therefore, no activation of beeper 46 results. When needle 32 is inserted through septum 18 against contact 20, circuit 22 includes a parallel resonant circuit. The circuit is completed from the needle to the contact plate through circuitry 22 to the common plate 24 and back through the skin of the patient to needle 32.

In the completed circuit, capacitor 40 is placed in parallel across coil 26. The value of coil inductance and capacitance will resonate at a certain frequency. This is the frequency that is preferably delivered by antenna 38. Many frequencies may be used to employ the present invention. Preferably, energy should be broadcast in the 100-200 kHz region.

After rectification by diode 42, current is applied to piezobeeper 46 and sound is emitted. Piezobeeper 46 may be any of the well known piezo devices, such as a sound device in the Medtronic Synchromed brand drug dispensers.

The sound is preferably generated by bursts of energy from antenna 38. Envelopes of bursts are preferably transmitted. If energy is transmitted in pulses of a particular frequency, such as 500 Hz, there will be a tone of that frequency. Envelopes of bursts are sensed so that a tone will be heard for the duration of the envelope. Therefore, intermittent beeps will result.

Figure 3:
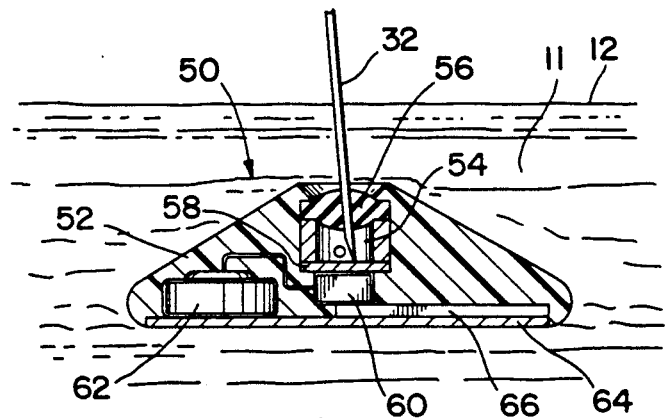
FIG. 3 is a cross-sectional view of an alternative embodiment of the present invention.

In FIG. 3, an alternative embodiment shows catheter access port 50 having a body 52 with a reservoir 54 closed by septum 56, as discussed above. A contact plate 58 is located in the bottom on reservoir 54, as discussed above. Contact plate 58 is electrically connected to circuitry 60, which is illustrated schematically. Also connected to circuitry 60 is battery 62, indifferent plate 64, and beeper 66.

The embodiment of FIG. 3 operates in a manner similar to that of FIG. 1, except that power is provided internally by battery 62 so that no broadcast of RF energy is required. Circuit 60 includes integrated circuit 68 similar to integrated circuits commonly used for controlling light emitting diodes. Inside the integrated circuit 68 is an electrode called the switch or a gate which is a high impedance unit. The integrated circuit is assumed to be CMOS so that it has very small current drain when there is no circuit connection. The circuitry employed for this is well known in the art.

Figure 4:
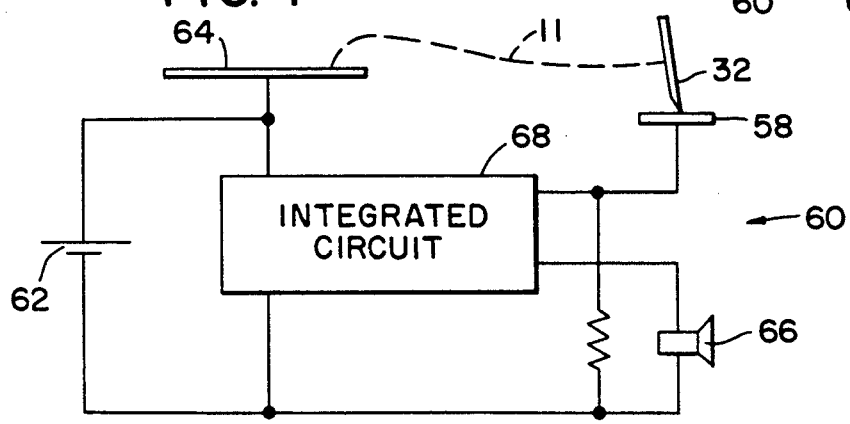
FIG. 4 is a schematic view of the circuit of the device of claim 3.

In FIG. 4, the circuit path, as discussed above, is from indifferent plate 64 through skin 12 to needle 32 and hence to contact 58. There is a potential voltage when the indifferent plate 64 is at the same potential as the contact 58. Integrated circuit 68 will then detect the fact that its gate is at the same potential and will start putting pulses from battery 62 to the piezobeeper 66. Sound will be emitted at the frequency of the pulses.

In this embodiment, the sound continues as long as the needle is in place and the drug is being administered. When the needle is removed, the circuit will go to low power and the device will wait for the next needle insertion. In alternative embodiments, the tone can be emitted for a time period and then shut off so that the tone is not continually sounding the whole time the needle is in the septum. While the invention is illustrated in terms of a catheter access port of the particular embodiment, it is understood that those skilled in the art can practice the invention to other various devices and embodiments.

What is claimed is:

1. An implantable medical device comprising:
   contact means for sensing contact with a percutaneous medical instrument including conductive contact means for contacting the medical instrument;
   means for providing power which is electrically connected to the contact means;
   means for generating an audible signal which is electrically connected to the contact means; and
   a conductive plate mounted on the device in contact with the patient's body and electrically connected to the contact means so that an electrical circuit includes a path from the plate through the body, through the medical instrument and back to the contact means.

2. The device of claim 1 wherein the means for providing power is an antenna for receiving radio frequency energy.

3. The device of claim 1 wherein means for providing power is a battery.

4. An implantable device having a reservoir for receiving medication from a percutaneously inserted hypodermic needle, the improvement comprising:
   a conductive contact plate mounted in the reservoir for electrical contact with the needle;
   circuit means mounted in the medical device and electrically connected with the contact plate;
   means for providing power to the circuit means mounted within the device; and
   a conductive external plate mounted exteriorly on the medical device in electrical contact with the circuit means so that a circuit may be completed from the needle through the contact plate, the circuit means, the external plate, the patient's body and through the needle back to the contact plate.

5. A drug dispenser for implantation in a patient's body having a reservoir for receiving medication from a percutaneously inserted hypodermic needle, the improvement comprising:
   conductive means mounted on the exterior of the device for electrical contact with the patient's body;
   circuit means mounted within the device in electrical contact with the exterior conductive means including means for generating and providing an audible signal; and
   means in the medical device for electrically sensing contact with the hypodermic needle, said sensing means being electrically connected to said circuit means, whereby an electrical circuit is completed through the needle, the circuit means, the exterior conductive means, of the patient's body enabling generation of the audible signal.

* * * * *